United States Patent
Zivin et al.

(10) Patent No.: US 10,780,296 B2
(45) Date of Patent: Sep. 22, 2020

(54) TRANSCRANIAL LASER THERAPY FOR TREATMENT OF ACUTE ISCHEMIC STROKE

(71) Applicant: Reni-Zoe Zivin

(72) Inventors: Justin Zivin, San Diego, CA (US); Luis De Taboada, Carlsbad, CA (US); Jackson Streeter, Gainesville, FL (US)

( * ) Notice: Subject to any disclaimer, the term of this patent is extended or adjusted under 35 U.S.C. 154(b) by 0 days.

(21) Appl. No.: 16/118,229

(22) Filed: Aug. 30, 2018

(65) Prior Publication Data

US 2019/0070431 A1  Mar. 7, 2019

Related U.S. Application Data

(60) Provisional application No. 62/553,296, filed on Sep. 1, 2017, provisional application No. 62/597,026, filed on Dec. 11, 2017.

(51) Int. Cl.
*A61N 5/06* (2006.01)
*H05K 1/11* (2006.01)
(Continued)

(52) U.S. Cl.
CPC ............ *A61N 5/0622* (2013.01); *A42B 1/242* (2013.01); *F21V 19/002* (2013.01); *F21V 29/70* (2015.01);
(Continued)

(58) Field of Classification Search
CPC .......... A61N 5/0622; A61N 2005/0652; A61N 2005/005; A61N 2005/0647;
(Continued)

(56) References Cited

U.S. PATENT DOCUMENTS 5,259,380 A  11/1993  Mendes et al.
6,063,108 A   5/2000  Salansky et al.
(Continued)

FOREIGN PATENT DOCUMENTS

EP      0130950 B1   4/1990
WO  2011115451 A2   1/2012
(Continued)

OTHER PUBLICATIONS

"The Treament Helmet for TBI / Concussion / CTE," Brain Thor, brainthor.com, accessed: May 2017. https://www.brainthor.com/.
(Continued)

*Primary Examiner* — Boniface N Nganga
(74) *Attorney, Agent, or Firm* — 21st Century IP LLC; Kelly Hollowell

(57) ABSTRACT

An apparatus and method of use for a comprehensive transcranial low-level light therapy for use with ischemic brain tissue using a multitude of polychromatic Light Emitting Diodes (LEDs) embedded into a flexible head covering that stretches securely around the patient's cranium to bath the entire cranium cavity in a variable frequency, variable power density light spectrum, maximizing all beneficial effects to the cellular tissues whether or not they are specifically deprived of blood from the ischemic stroke event. The bulbs covering the n-p junction of the semiconductor LEDs directly contact the patient's cranial skin to maximize the depth of penetration of the wavelengths into the brain's cortex cells. By using many individual point-source LEDs emitting all around the cranium, greater therapeutic benefit can be achieved as more of the cortex tissues are irradiated.

3 Claims, 5 Drawing Sheets

(51) Int. Cl.
*H05K 1/02* (2006.01)
*A42B 1/24* (2006.01)
*A61N 5/00* (2006.01)
*H05K 1/03* (2006.01)
*H05K 1/18* (2006.01)
*F21V 29/70* (2015.01)
*F21V 19/00* (2006.01)
*F21Y 115/10* (2016.01)

(52) U.S. Cl.
CPC ......... *H05K 1/0203* (2013.01); *H05K 1/0393* (2013.01); *H05K 1/115* (2013.01); *H05K 1/182* (2013.01); *A61N 2005/005* (2013.01); *A61N 2005/0647* (2013.01); *A61N 2005/0652* (2013.01); *A61N 2005/0659* (2013.01); *F21Y 2115/10* (2016.08); *H05K 2201/10106* (2013.01)

(58) Field of Classification Search
CPC ........... A61N 2005/0659; H05K 1/182; H05K 1/0393; H05K 1/115; H05K 1/0203; H05K 2201/10106; F21V 29/70; F21V 19/002
See application file for complete search history.

(56) References Cited

U.S. PATENT DOCUMENTS

| | | | |
|---|---|---|---|
| 6,402,678 | B1 | 6/2002 | Fischell et al. |
| 6,537,301 | B1 | 3/2003 | Kamei |
| 6,618,614 | B1 | 9/2003 | Chance |
| 6,896,693 | B2 | 5/2005 | Sullivan |
| 6,918,922 | B2 | 7/2005 | Oron |
| 7,575,589 | B2 | 8/2009 | De Taboada et al. |
| 7,850,720 | B2 | 12/2010 | Shefi et al. |
| 8,308,784 | B2 | 11/2012 | De Taboada |
| 8,316,860 | B1 | 11/2012 | Porter et al. |
| 9,457,201 | B2 | 10/2016 | Hoelscher et al. |
| 9,610,460 | B2 | 4/2017 | Huttemann et al. |
| 2003/0109906 | A1 | 6/2003 | Streeter |
| 2010/0076527 | A1* | 3/2010 | Hammond ................ G09F 9/33 607/88 |
| 2010/0204762 | A1 | 8/2010 | De Taboada et al. |
| 2011/0092863 | A1* | 4/2011 | Kim .................... A61N 5/0617 601/18 |
| 2011/0144723 | A1* | 6/2011 | Streeter ............... A61N 5/0618 607/88 |
| 2014/0088668 | A1 | 3/2014 | Kim et al. |
| 2014/0128942 | A1* | 5/2014 | Bembridge ......... A61N 5/0613 607/90 |
| 2015/0246240 | A1* | 9/2015 | Huttemann ......... A61N 5/0613 607/89 |
| 2016/0008628 | A1 | 1/2016 | Morries et al. |
| 2016/0030001 | A1 | 2/2016 | Stein et al. |

FOREIGN PATENT DOCUMENTS

| | | | | |
|---|---|---|---|---|
| WO | 2012024243 | A1 | 2/2012 | |
| WO | 2016151377 | A1 | 9/2016 | |
| WO | WO-2017019839 | A1 * | 2/2017 | ........... A61N 5/0616 |

OTHER PUBLICATIONS

"Salon Laser Helmet Hair Loss Therapy Laser Hair Treatment for Baldness," ZJKC, lasertherapy-device.com, Model No. LCAP154, accessed: May 2017. http://www.lasertherapy-device.com/sale-7655434-salon-laser-helmet-hair-loss-therapy-laser-hair-treatment-for-baldness.html.

Gefvert, Barbara, "Medical Lasers/Neuroscience: Photobiomodulation and the brain: Traumatic brain injury and beyond," Bio Optics World®, biooticsworld.com, May 9, 2016. http://www.biooticsworld.com/articles/print/volume-9/issue-5/medical-lasers-neuroscience-photobiomodulation-and-the-brain-traumatic-brain-injury-and-beyond.html.

"What is TransCranial Light Therapy," Care Electronics, Inc., transcraniallighttherapy.com, accessed: May 2017. http://transcraniallighttherapy.com/.

* cited by examiner

TRANSCRANIAL LASER THERAPY FOR TREATMENT OF ACUTE ISCHEMIC STROKE

CROSS REFERENCE TO RELATED APPLICATIONS

The present application claims priority benefit of U.S. Provisional Application No. 62/553,296, filed Sep. 1, 2017, and it claims the priority benefit of U.S. Provisional Application No. 62/597,026, filed Dec. 11, 2017, the contents of which are herein incorporated by reference in their entirety.

FIELD OF INVENTION

This invention generally relates to methods of treating human tissue injuries and promoting healing using visible and infrared frequency, low-energy lasers and other light sources. Embodiments of the disclosure presented here relate to treating ischemic stroke patients using low-energy lasers aimed directly onto a patient's outer cranial tissues. When the laser beam contacts the patient's cranial skin, some of the laser's light frequencies, penetrate below the skin beyond the cranial bones and up to a few centimeters into the brain tissue itself. These penetrating frequencies are most often the longer wavelength infrared and near infrared frequencies. Generally, the use of light frequencies to stimulate living tissues is referred to as photobiomodulation (PBM) or Low-Level-Light Therapy (LLLT). LLLT can employ low-power lasers or light-emitting diodes (LEDs) to generate the light frequencies desired. When LLLT is applied to the brain, it is known as transcranial LLLT (TLLLT) or transcranial PBM (TPBM).

BACKGROUND OF THE INVENTION

With respect to ischemic stroke patients (i.e., strokes caused by blood clots), physicians typically divide them into two categories based on the source of the blood clot. Embolic stroke occurs when the clot forms outside of the brain tissue and is brought into the brain through its vascular network. Thrombotic stroke occurs when the clot itself forms within the brain's vascular network due to diseased or damaged arteries. In either mechanism, the clot causes a sudden loss of blood flow to the brain cells, which deprives them of oxygen, nutrients, and waste removal services necessary to healthy cellular function. Cellular necrosis gradually progresses in the hours after the blood flow loss begins. The rate of cellular necrosis of brain tissue after a stroke onset will invariably exceed the body's natural revascularization processes, which work to bypass the blockage and return blood flow to the affected tissues.

The FDA has approved additional mitigating therapies that can both slow the rate of cellular necrosis after stroke onset and catalyze these natural revascularization processes. However, for most stroke patients, some permanent loss of brain tissue will occur because of the lapse of time between initially detected symptoms and how quickly mitigating efforts can be implemented such as at an emergency room or other medical treatment facility. Because time is always "of-the-essence" for mitigating permanent or long-term damage to brain tissues after stroke onset, medical personnel often cannot perform extensive diagnostics on a patient's cranial volume to identify the exact location of the blockage, the type stroke that has occurred and the brain tissues likely to be most affected by the blood loss. As a result most aggressive tactics for slowing the rate of cellular necrosis, removing or bypassing the clot or accelerating revascularization are impractical. What is needed is a tool that can more quickly bring beneficial stimulation to the entire outer cortex of the brain to directly slow the rate of cellular necrosis so that chemical blood therapies or, in some cases, surgical intervention will have more time to work or be implemented before permanent or long-term tissue damage occurs.

With regard to how TLLLT affects brain cells, studies have shown that TLLLT stimulation increases the rate of neurogenesis, promotes higher levels of brain-derived neurotrophic factor (BDNF) and nerve growth factor (NGF), measurably reduces levels of inflammation, increases rates of blood flow, reduces pain by increasing the rate of natural opiate release within the tissues, increases the rate of oxygen consumption in the frontal cortex, and increases blood serotonin levels.

Generally, light wavelengths of between 632 nanometers (nm) and 1064 nm can cause beneficial stimulation of biological cells. For brain cells, the optimal range appears to be between 800 nm and 1000 nm; these wavelengths are more effective at penetrating the soft cranial tissues and the skull to reach the cells of the brain's outer cortex region. Although generally the mechanisms by which these light frequencies interact with cells in a positive manner are not fully understood, some researchers speculate that biological cells exposed to this light undergo certain photochemical reactions that accelerate natural healing processes and speed recovery time for a damaged cell to return to normal function. One interesting theory suggests LLLT fundamentally stimulates a cell's mitochondrial ATP energy cycle resulting in more chemical energy available for a damaged cell to repair itself. Cellular mitochondria appear to contain monochromatic photoacceptors that can absorb specific photon frequencies from light and convert them into ATP, which is the primary chemical energy form that drives cellular function and biological processes. This mechanism would be somewhat analogous to how plants use photosynthesis to build their tissues from solar photon exposure. Although most internal human cells do not directly use sunlight, the biological "hardware" for using sunlight as a cellular energy source appears to be in place. TLLLT could be one way in which a cell that has lost access to blood flow might be able to temporarily generate energy to function until the blood flow returns via natural revascularization processes. A cell may also contain any number of other monochromatic photoacceptors that could drive other cellular reactions and functions in the temporary absence of blood flow.

Since 1967, many medical studies have been conducted using TLLLT that show verifiable benefits to patients and virtually no observable harmful side effects. Because the energy level of the TLLLT lasers are in the mW/cm2 range, they do not cut or burn tissues, but rather stimulate a biological response and encourage improvements in cell function. In one clinical study, TLLLT was applied over the entire cranial surface of stroke patients approximately 18 hours after their stroke. Five days after the stroke, the TLLLT-treated patients showed measurable improvement in stroke recovery compared to the untreated control group. Measurable improvements from just one TLLLT treatment continued even 90 days after the stroke. This clinical study concluded that 70% of stroke patients treated with TLLLT had permanent measurable improvement in brain function compared with only 51% of the control group patients.

Current research using TLLLT is mostly conducted on rats and rabbits, which have also shown measurable improvements in neurological function and behavior from TLLLT. Recent experiments have confirmed that TLLLT resulted in the growth of new brain cells in these animals, which improved their overall recovery rates. To assist researchers in gauging the results of their TLLLT experiments on the animals, certain models are created, such as the Rabbit Small Clot Embolic Model (RSCEM). Although earlier experiments using this model have shown clinical improvements in the rabbits using TLLLT, optimal timing and dosing has yet to be fully known or understood.

In one RSCEM study, a dose-escalating regimen was tested. Behavioral analysis was then conducted at 24 hr post-treatment (embolization), which allowed the researchers to determine the effective stroke dose (P50) or clot amount (mg) that produces neurological deficits in at least 50% of the rabbits exposed to treatment. For the RSCEM model, a treatment is considered beneficial if it significantly increases the P50 compared with the control group. For this study, a significant behavioral benefit was seen using a 111 mW laser treatment of 2 minutes at 2 hours post-embolization, which was an improvement over previous dosing regimens examined. In another RSCEM study, researchers demonstrated long-term behavioral improvement with TLLLT when treating animals at 3 and 6 h after cerebral embolization.

For rats, an alternate model was developed called the Middle Cerebral Artery Occlusion (MCAO) model. One MCAO study demonstrated that TLLLT applied at 24 h after the ischemic injury produced a significant improvement of the neurological severity score as compared with the controls when measured 14 days after the stroke. A later MCAO study successfully duplicated these results.

For human patients, studies have shown safe, beneficial effects when TLLLT is applied as a single treatment within 24 hours after the stroke onset. In two recent clinical human trials, safe treatment was demonstrated in acute ischemic stroke patients. Both trials showed a reduction in long-term disability as measured by the Modified Rankin Scale (MRS), which ranks symptoms of stroke patients from 0 (no symptoms) to 6 (terminus). However, the optimal timing and the irradiation dose for acute ischemic stroke patients have yet to be determined. Some studies have shown an incremental benefit of TLLLT with higher irradiation power and energy levels. However, merely applying additional laser energy can have minimal or no effect on the target tissue. Also, over-radiating can damage the tissue from thermal effects.

Most of the TLLLT animal studies have shown better efficacy when applied sooner after the ischemic injury onset rather than later. At some delayed point, any efficacy from TLLLT therapy is not observed. TLLLT appears to be equally effective when applied at different times within the first 24 h of the ischemic injury onset although further work needs to be done in this area. Some researchers have suggested that TLLLT may photomodulate at different stages of the brain ischemic cascade. However, in three of the most recent clinical trials conducted using primitive TLLLT devices (too low power, too high duty cycle, too few laser exposure points, etc.), only one trial was statistically significant, while one had a P50 equal to 0.09. The third trial was completely negative in terms of demonstrating benefits. What is needed in the art is a better more consistent way to deliver the TLLLT energy in a more consistent and effective way to a patient. Prior studies only exposed human patients to TLLLT at up to 20 points around the skull; and exposure times were limited to 2 minutes each.

More specifically, what is needed is a helmet, bathing cap, or wearable head covering with a large TLLLT or other light source coverage area to maximize the tissue exposure. Subsequent dosing studies have found that prior TLLLT studies used lasers that were 1/10th as powerful as therapeutically warranted based upon the data observed. Moreover, the exposure frequencies were 1/60th as short as is therapeutically warranted. TLLLT devices that focus on a relatively narrow or limited area typically require specific knowledge as to where the oxygen-starved tissues exist in the patient's cranial volume, which is not always practical or optimal for a post-ischemic stroke patient. Since both healthy and distressed brain cells can benefit from TLLLT, a better way of protecting distressed cells is to immediately expose the maximum amount of cortex brain cells to therapeutic light frequencies at the earliest possible time after onset of symptoms. By avoiding the time required to identify the specific ischemic area of the cortex involved, the patient can gain valuable time in protecting the distressed brain cells while at the same time stimulating the brain cells that are not in immediate distress.

What is still further needed in the art is an improved therapy over the FDA-approved endovascular treatment therapies stroke patients, which has no adverse side effects, does not need extensive laboratory safety testing or FDA pre-approval, and requires no special training to implement.

What is further needed in the art is a practical and effective device for applying TLLLT in the post-ischemic stroke environment at the earliest possible moment and continue periodically as the patent is moved to a treatment center.

SUMMARY OF THE INVENTION

As conventional TLLLT methods of treatment involve using a hand-held medical laser device, treatment protocols typically are labor intensive, time consuming and target a relatively small area of brain tissue. In the practical clinical environment, patients often must first undergo diagnostic testing so that the location of the ischemic event can be detected. Only then can the limited coverage area of hand-held medical lasers be directed to the damaged tissues. Moreover, to enhance the radiant intensity of laser light that penetrates the cranium and reaches the cortex tissues, the laser wand typically must be pressed directly against the patient's skin and moved around the area of ischemia. These practical factors have limited the attractiveness and the effectiveness of TLLLT, limiting ischemic patients to only conventional chemical and blood therapies to improve their condition.

The present disclosure provides a novel apparatus and method of use for a comprehensive TLLLT radiative environment over the largest area of the cranium that can greatly slow the level of brain cell necrosis in post-ischemic stroke patients. Secondly, the present invention also provides significantly greater exposure of the outer brain cortex to more wavelengths of light and at higher power levels without posing any adverse effects to the underlying cellular tissues. The invention brings multiple mitigating measures to ischemic stroke patients from stabilizing and supporting cells that have lost blood flow to catalyzing natural revascularizations processes of tissues that have not lost blood flow, which allows stroke patients to recover faster and have fewer long-term symptoms throughout the healing process.

In one embodiment of the current invention, a multitude of polychromatic Light Emitting Diodes (LEDs) are embedded into a flexible head covering that stretches securely around the patient's cranium to bath the entire cranium cavity in a variable frequency, variable power density light spectrum, maximizing all beneficial effects to the cellular tissues whether or not they are specifically deprived of blood from the ischemic stroke event. The bulbs covering the n-p junction of the semiconductor LEDs directly contact the patient's cranial skin to maximize the depth of penetration of the wavelengths into the brain's cortex cells. By using many individual point-source LEDs emitting all around the cranium, greater therapeutic benefit can be achieved as more of the cortex tissues are irradiated. Because infrared light of this type poorly penetrates air, in one embodiment, it is important that the medical lasers or LEDs directly contact the skin.

DETAILED DESCRIPTION

Figure 1:
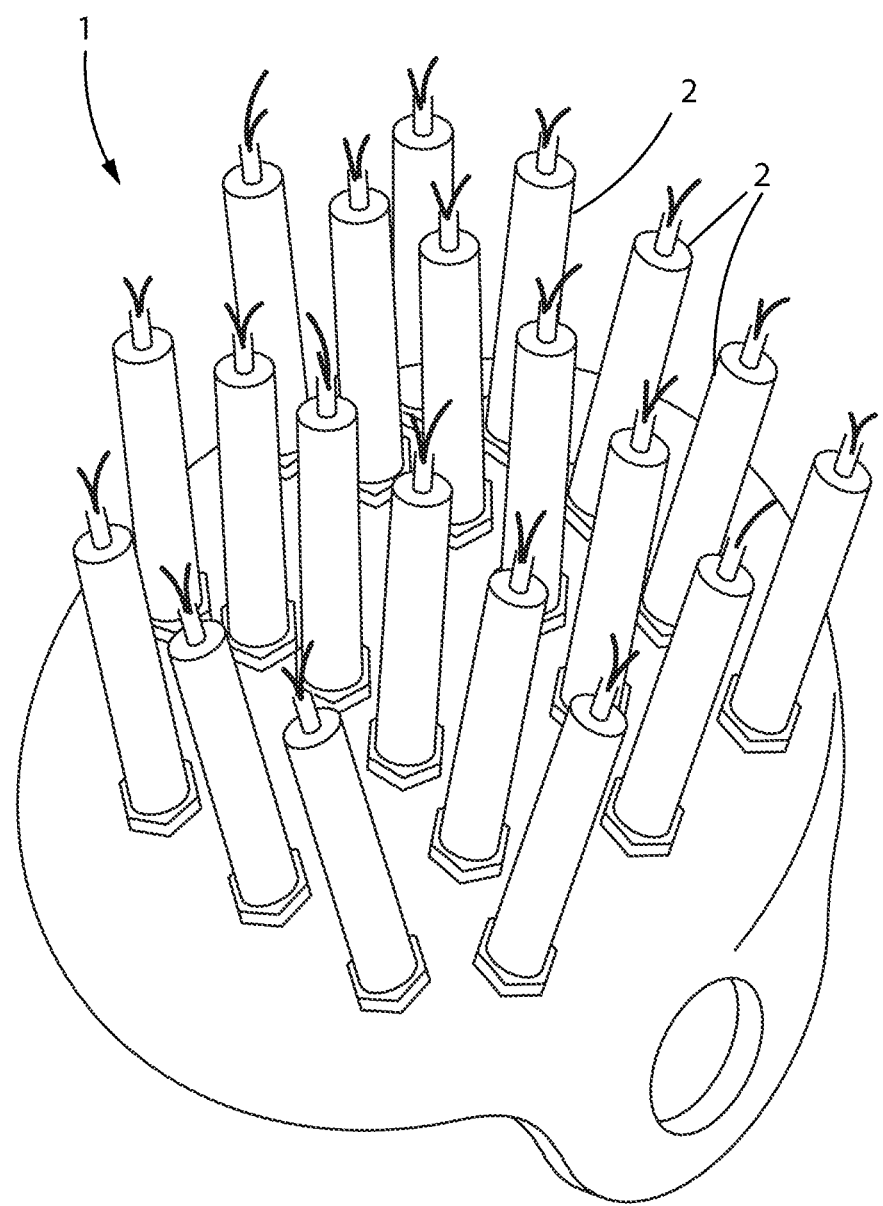
FIG. 1 shows a head covering with attachment points for plurality of Aculaser wands.

In reference to FIG. 1, the current invention comprises a head covering device 1 that greatly increases the area of a patient's cranium exposed to therapeutic TLLLT frequencies. The most therapeutic light frequencies so far identified for ischemic patients are between 730-970 nm. Current TLLLT protocols incorporate hand-held, narrow-beam conventional medical lasers pointed directly at the affected brain tissues by a technician after diagnosing the location of the ischemic event. However, because TLLLT has been shown to be safe for both healthy and ischemic tissues, irradiating more of the cortex surface area with light in this frequency range, at higher radiant intensity, and for longer periods of time, will provide greater therapeutic benefit to ischemic patients. As a practical matter, hand-held medical lasers simply cannot provide the best level of exposure time and intensity for most ischemic patients. In one embodiment of FIG. 1, a head covering device 1 is provided that can hold a plurality of conventional medical lasers 2 in place around the brain tissue so that the patient can be irradiated for longer periods of time. The position of the laser wands can be adjusted around the patient's cranium by a technician during treatment protocols, or if the specific location of the ischemia is known, the number of available lasers can be directed to that area of the brain.

Figure 2:
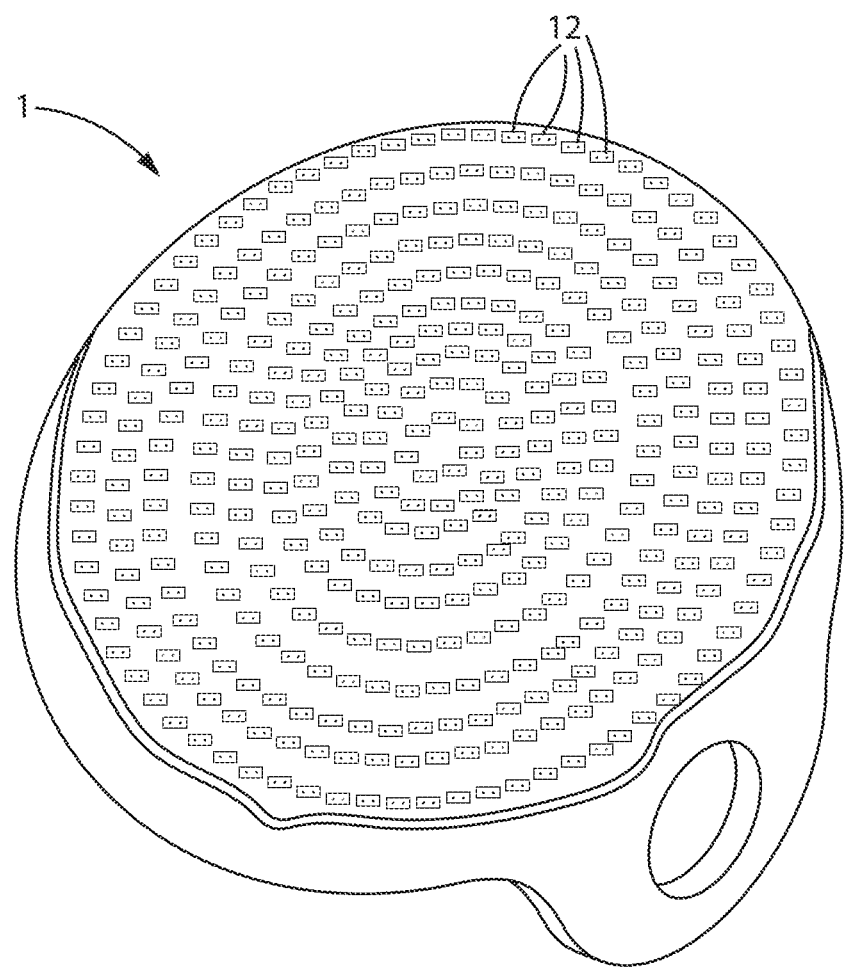
FIG. 2 shows an angled side view of a head covering showing an inner liner with an LED array.

Alternatively, FIG. 2 shows a head-gear assembly comprised of a plurality of LED lasers 12 that irradiates the entire cranial cavity without first needing to know where the ischemic tissues are located. Both conventional medical lasers and LED lasers can project radiant intensities between 200 mW/cm2 and 600 mW/cm2, which has been shown to be most therapeutic for ischemic brain tissues. Silicon, Gallium Arsenide and Cadmium Selenide LEDs are known to produce frequencies in the infrared and near infrared range. For example, Excelitas Technology's PGEW Series of LEDs can produce 905 nm light at peak power rates of up to 100 Watts. However, since the overall radiant intensity a patient is exposed to is a function of the laser's output power per the area of cranium exposed, then employing many LEDs of lower power output, can provide the same overall intensity as a single larger laser pointed at a smaller area of the cranium. In one embodiment, the medical lasers or LED lasers project 808 nm light at a peak power rate of 110 watts.

Figure 3:
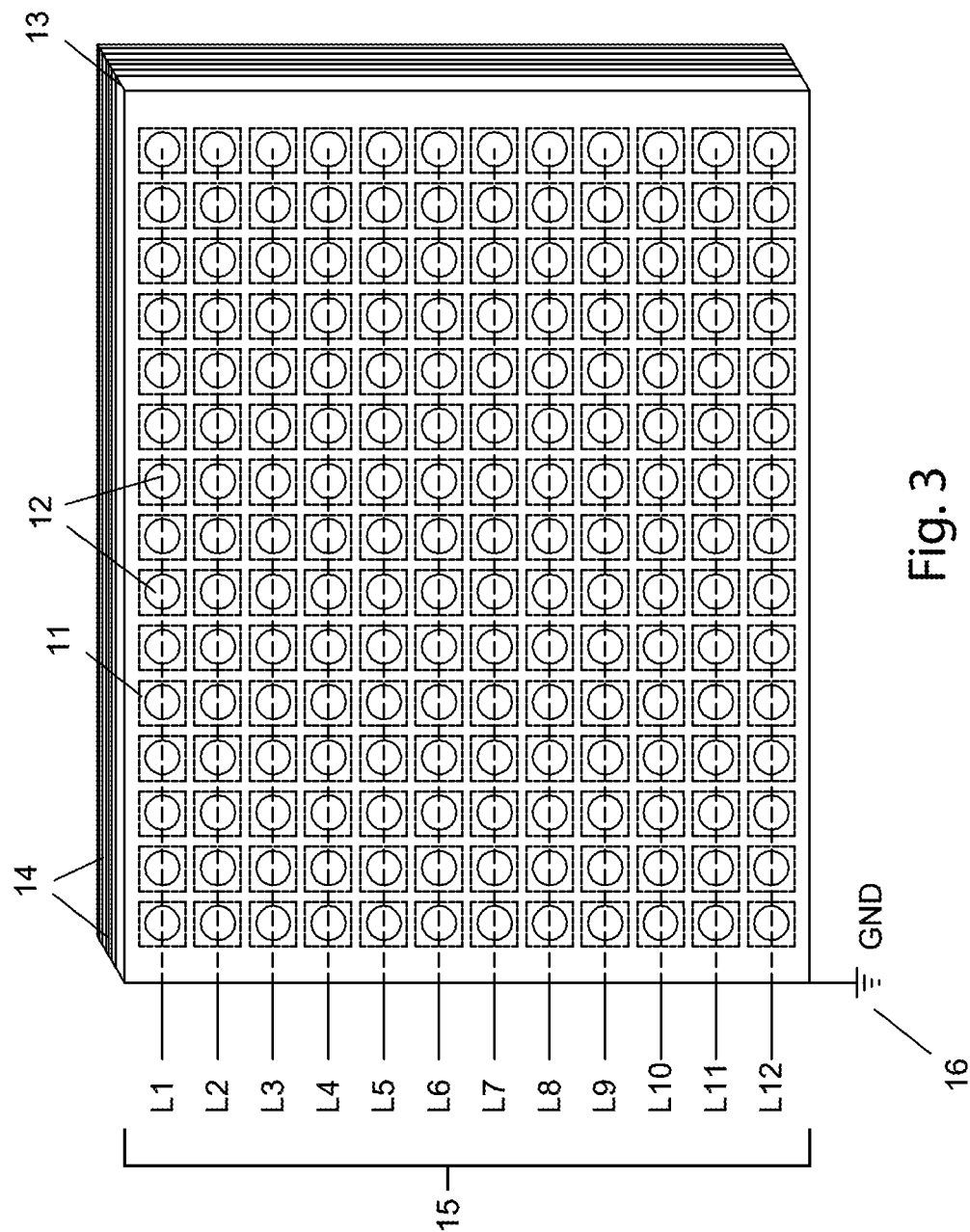
FIG. 3 shows a flat sheet LED array showing the soft inner layer, LED array, and multi-layer rigid-flex PCB substrate and interconnecting wiring.

In reference to FIG. 3, a large array of LEDs 12 is embedded into a flexible substrate that can be fitted on to a patient's cranium. Such an array could be comprised of a plurality of dense matrix LEDs, 1-mm2 Surface Mount Devices, or 5 mm Thru-hole bulbs depending on the LEDs power specifications. In one embodiment of this array, the LEDs 12 are inserted into a stretchable silicone sheet 13 that forms the inner layer of the head cover contacting the patient's cranium. This flexible inner layer holds the individual LED bulbs directly onto the patient's skin, while the layer material between the bulbs also contacts the skin and helps relieve any point-pressure caused by the bulbs. In one embodiment, this flexible inner layer is made from a soft silicon, silicon composite or material of similar physical properties. Behind this inner bulb layer is a multi-layer high-density interconnect printed circuit board (PCB) 14 with microvias for receiving a pair of terminals (+/−); each of the two LED terminals, are soldered or connected to specific conducting strips within the interconnect PCB 14. One of each pair of the terminals for each LED is connected to a lead wire 15 that connects to a DC power supply (not shown). There can be multiple lead wires depending on the number of layers, as shown in FIG. 3 as L1 through L12. The other terminal for each pair of terminals for each LED is connected to a common ground 16 that returns the current flow back to the power supply. The number of leads and the number of LEDs wired to each lead are determined based on desired electrical designs and the specifications of each type of LED selected for the array. In one embodiment, the array is made up of a plurality of LEDs that emit different frequencies within the therapeutic ranges defined and are distributed evenly within the array matrix. In another embodiment, the multi-layer interconnect PCB is comprised of a plurality of rigid PCB segments 11 that are connected together using flexible conductor boards so that the PCB layers can expand with the stretchable inner layer while maintaining the integrity of the conductor pathways.

Figure 4:
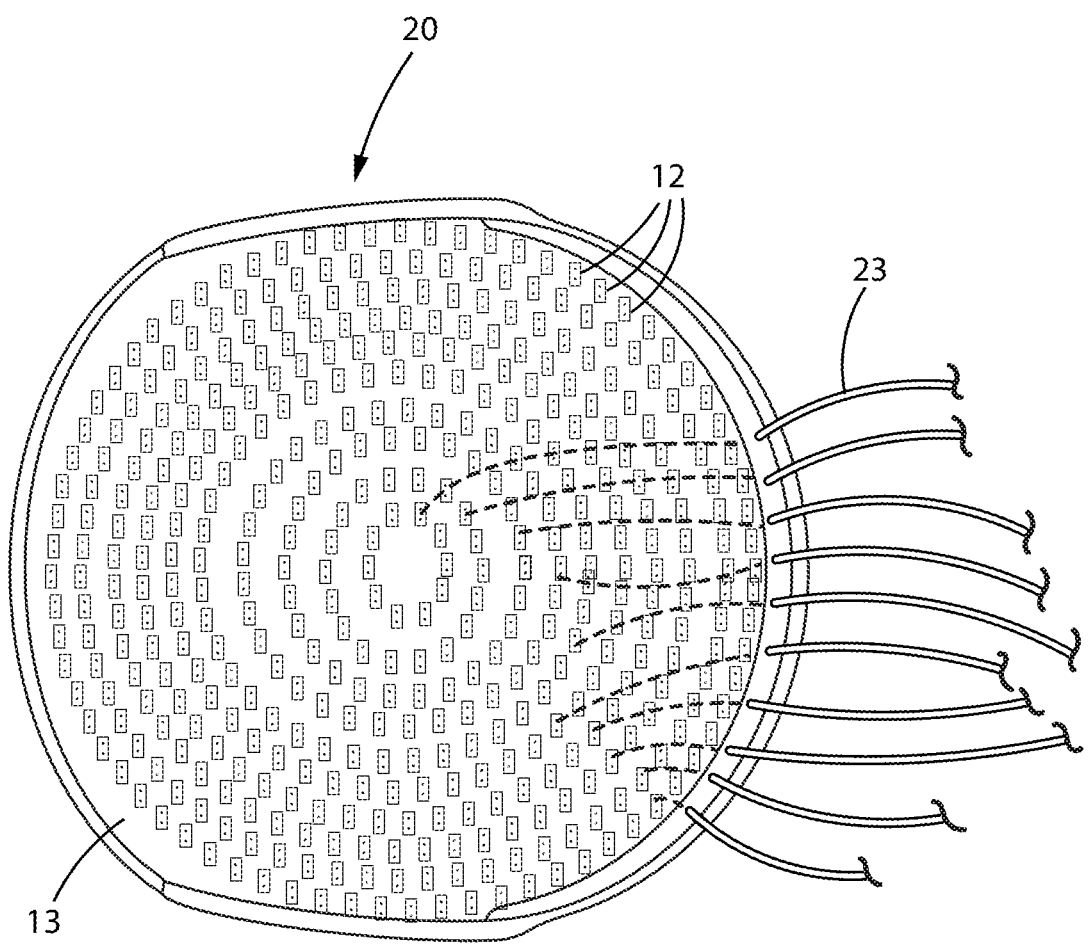
FIG. 4 shows an underside view of the head covering shown pressed into the inside of the head covering with termination leads in the bottom rear of the cover.

In reference to the embodiment of FIG. 4, the flexible LED array is pressed into and secured to a protective head covering unit 20 that is then placed over the patient's head similar to a helmet or a bathing cap. A plurality of power leads 23 connected to the conductors of the interconnect PCB terminate at the rear base of the head covering for connection to the unit's power supply. In one embodiment, the plurality of leads terminating at the rear base of the head covering unit 20 correspond strings of LEDs of a common emitting frequency in parallel to the power supply (frequency grouping). In another embodiment, not shown, the leads connect to strings of variable frequency LEDs based on the overall power draw of the string (power grouping). In another embodiment, an LCD-type array (i.e., an LCD matrix that controls individual or groups of LEDs within the head covering using an external microprocessor circuit with sophisticated protocols similar to playing a movie on an LCD screen with the "R-G-B" pixels being groups of different wavelength emitting LEDs forming the equivalent of moving images across the inside of the head covering) is incorporated into the LED matrix where each individual LED is controllable like a RGB pixel array. In this embodiment, groups of LEDs of a common or different emitting frequency can be grouped together and activated by a computerized power supply. In one embodiment, the power is wirelessly transmitted from the unit's power supply to the head covering unit. In one embodiment, in a RGBA Color Space, the head covering can be controlled with at least 4 bits: R, G, B, Alpha (A), where Alpha is the "opacity" bit that instructs a pixel group to have shadowing capability. In such an embodiment, the head covering is comprised of at least three different LEDs, each emitting a different wavelength (720-750 nm, 820-850 nm, 900-940 nm) with the Alpha bit being "power intensity" (a number between 0 and 1, 1 being the maximum LED intensity). In such an embodiment, LCD-type microprocessors and controllers can drive the TLLLT protocol for the LEDs in the head covering device by adapting the LCD drivers to a multi-component LED array so that existing digital video editing software and rendering engine media servers can be used to program and drive head covering's power supply and TLLLT protocols.

In reference to the embodiment of FIG. 4, the types of LEDs incorporated into the array vary in the emitting wavelength across the therapeutic range, generally found to be between 700-1000 nm. In one embodiment, the array is comprised of blend of commercially available 850 nm LEDs with a 45 nm bandwidth and 905 nm LEDs with a 15 nm bandwidth. Alternatively, custom LEDs specially lensed to the therapeutic ranges identified can be used individually or in any combination desired. In another embodiment, the overall radiant intensity of the LED array controllable either by the power supply feeding the LEDs or the selected combination of individual LEDs comprising the array. For ischemic stroke patients, the therapeutic radiant intensity is between the range of 200 mW/cm2 and 600 mW/cm2 inclusive. Although other therapeutic benefits to other tissues may lie in lower radiant intensities, the highest risk to the tissues lies in the higher radiant intensity range as the light frequencies can cause thermal heating of the tissues.

In one embodiment of the current invention, the overall radiant intensity of the device is controlled by regulating the current flow to the individual LED elements comprising the array. In another embodiment, the number of emitting LEDs over the total coverage area is varied to control the effective radiant intensity. Generally, the higher the radiant intensity emitted from an LED, the higher level of waste heat that must be removed from the LED so that the LEDs temperature remains within the design operating range. Overheating the LEDs will cause the frequency emitted to deviate from the desired range, cause premature failure of the LED, and may become uncomfortable to the patient being treated. The multi-layer PCB can incorporate special layers that operate as heat sinks that remove the waste heat from the bulb itself and dissipate that heat externally. Commercially available dense matrix LEDs have built-in, localized heat sinks that dissipate heat away from the LEDs emitting bulb. Alternatively, for some LED designs, the "duty-cycle" is limited to very short durations to allow waste heat to dissipate without causing the LED to exceed temperature limits. For LEDs with a maximum duty cycle (non-continuous LEDs) heat management within the LED array can be controlled by grouping LEDs in rapid on/off cycles around the patient's cranium to simulate near continuous irradiation during the treatment protocol. In another embodiment, some or all of the LEDs are pulsed on/off at high frequencies per their design duty cycle.

In continued reference to FIG. 4, better therapeutic benefit of TLLLT occurs with the light sources pressed comfortably against the cranial skin with the patient's hair removed. Since adult human crania have dimensional variability between both men and women, the device will need to have some flexibility to accommodate this natural cranial dimensional variability. However, the flexibility of any PCB circuit is limited due to the need for conductor continuity between the LEDs and the power source. In one embodiment, the head covering has an effective spheroid radius of at least 4.3 inches and is stretchable outward by up to 0.25 inches to accommodate the largest range of percentiles between both men and women. In another embodiment, the device is comprised of plurality of head-covering sizes selected for a given patient and attached to the power supply after placing on the patient's head. Equivalent spheroid radius of male skulls ranges from 4.3-4.7 inches from 50th to 99th percentile. Equivalent spheroid radius of female skulls ranges from 4.1-4.5 inches from 50th to 99th percentile.

An objective of certain embodiments of the current disclosure is to irradiate maximum possible area of the patient's cranium as soon as symptoms occur rather instead of first locating the tissues affected and just focusing light to the tissues in that area. Generally, the most therapeutic benefit for ischemic patients can be achieved by the combination of exposure duration and light intensity. In one embodiment, the invention incorporates a basic power supply with low-cost LEDs that can be used by first responders, ambulances and emergency rooms who initially receive ischemic patients. In another embodiment, a low-cost irradiation device with a disposable cap (i.e., a head covering) can be stored on airplanes or workplaces, similar to defibrillators, which can be quickly applied to patients immediately once symptoms appear. In a further embodiment, more sophisticated LEDs with a variable output power supply can be used in ischemia treatment centers and physician's offices to provide more advanced TLLLT protocols.

In one study, a single TLLLT treatment within 24 hours after the ischemic event occurred showed measurable patient benefit. Subsequent analysis of TLLLT studies seem to indicate that multiple light treatment can effectively photo-modulate at different stages of the ischemic cascade. In another study, exposure of animals starting 2 hours after an ischemic event lasting 6 minutes showed measurable positive benefit with a radiant intensity as low as 7.5 mW/cm2 using an 808 nm light frequency. Still in another study, cycles of exposure of lasting 2 minutes at 2 hours, 3 hours, and 4 hours after the ischemic event showed measurable benefits with a radiant intensity of 111 mW/cm2 and 1,000 nm laser. Generally, these studies show that early exposure of the cortex tissues with infrared light provides benefit to patients, but that benefit decreases over time after the ischemic event. However, other studies at lower radiant intensities have been inconclusive as to beneficial results. Higher radiant intensities, above 200 mW/cm2 were thought to be avoided as the risks to damaging the cells from thermal effects increased. However, this danger was found largely to be due to exceeding the duty cycle of the laser and distortion of the emitted frequency from the intended design into longer infrared wavelengths that are better carriers of heat energy into the tissues. By incorporating a multitude of emitting point sources across a broader surface area of tissue, more tissue can be irradiated without requiring higher and higher powered lasers operating beyond their design duty cycles. By incorporating a variable output power supply and a broader range of emitted frequencies, more sophisticated TLLLT protocols can be developed and customized to the type and magnitude of ischemia and the overall age and health of the patient. By exposing ischemic patients with a higher radiant intensity of light and earlier after the onset of symptoms, greater benefits can be delivered to the patient by the medical community.

Clinical benefits to ischemic stroke patients can generally be organized into two mechanisms: 1) stabilizing the oxygen-deprived cells from further damage and 2) enhancing the natural revascularization processes to return blood flow to the affected tissues. In one TLLLT study, a mechanism for this first benefit was theorized to involve inhibiting the formation of Cytochrome c Oxidase, an enzyme believed to increase the rate of cellular morbidity. This study concluded that certain wavelengths of IR light stimulate mitochondrial photoreceptors that stabilize the cell until the flow of oxygen and nutrients returns. However, the only current FDA-approved therapy for ischemic stroke involve injecting clot-breaking medicines into the patient's bloodstream to try and speed up the second benefit. An objective of the current invention is to irradiate both the ischemic cells to stabilize their biofunction while at the same time irradiating frequencies to healthy tissues to accelerate the natural revascularization processes. The complexities of the interactions between various light frequencies and thousands of cellular chemicals and structures is extremely difficult to determine with any degree of confidence. Therefore, exposing the patient's healthy and damaged brain cells to as many potentially therapeutic frequencies as soon as symptoms are detected approaches healing from all potential TLLLT directions. Furthermore, because TLLLT has no discernable side effects to the patient, this "all-of-the-above" approach to treatment using embodiments of the current disclosure, all maximum benefits to the patient can be realized.

In continued reference to FIG. 4, by placing the head cover around the back of the patient's cranium, and by pointing the light sources directly inward toward the patient's cranium, there is less risk of exposing the patient's eyes with harmful frequencies of light. Conventional TLLLT protocols require trained technicians to point one or more hand-held lasers directly on to the ischemic tissues. Because infrared light, especially concentrated light in a narrow beam, is dangerous to photoreceptor cells on the back of the eye, special care must be taken to shield the patient during TLLLT treatment. This limitation also affects the maximum exposure time a patient can receive and excludes brain tissues behind the eye area from receiving treatment. In the current invention, the lasers are pointed directly into and all around the cranial cavity in a fixed position that does not require movement or "striping" of the affected tissues by a technician wielding a hand-held laser. In one embodiment, a light-reflective barrier lines the face-rim of the head cover to ensure no infrared light escapes the head cover area. Also, the shape of the head cover profile maximizes the safe coverage area behind and around the eyes, which maximizes the reachable area of cortex tissues. The embodiment of the current invention is both safer for the patient and safer for the medical personnel to operate.

Figure 5:
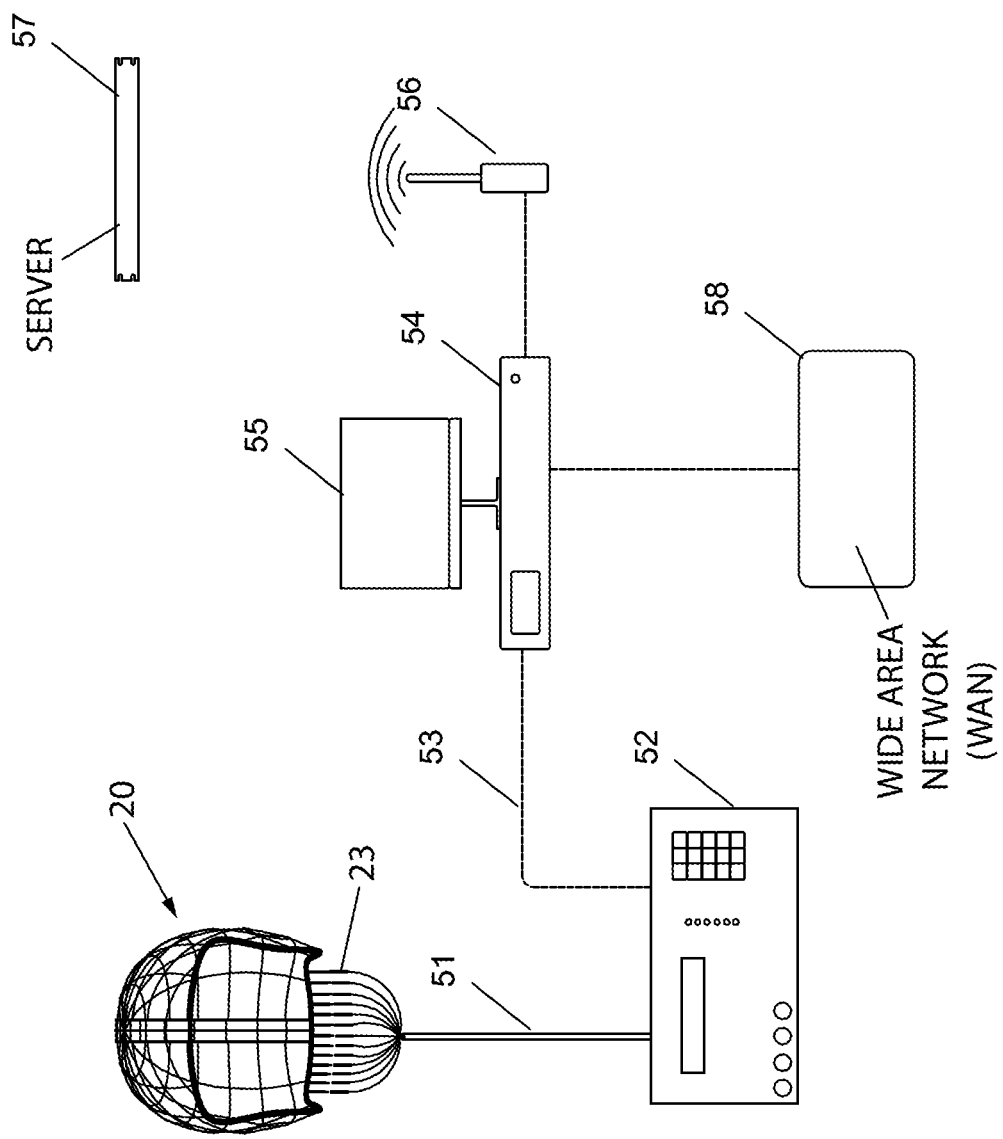
FIG. 5 shows a diagram of an interconnected head covering, wiring harness, power supply, microprocessor, HMI control application, wireless interface to treatment facility and wide-area network communication links.

In reference to FIG. 5, in one embodiment of the current disclosure, the leads 23 of irradiating head cover 20 are connected to a power supply 52 by a multiconductor cable 51, which is also connected to the power supply 52. The power supply 52 is connected to and controlled by a microprocessor 54 via a USB cable 53 or other electronic connector. The microprocessor 54 executes a Human Machine Interface (HMI) application 55 that allows the physician to select various operating parameters of the connected devices, such as patient exposure time, power radiance and other TLLLT protocol variables. In one embodiment, the HMI application is preconfigured to accommodate the technical specifications of the power supply and the LED array being fitted on to a patient. In another embodiment, the power supply 52 is directly configurable for the LED array and can implement various TLLLT protocols without needing connection an HMI control application. In either embodiment, multiple TLLLT protocols can be preconfigured to include more than just ischemia treatment regimens, but may be configured for other therapies, such as concussions, post-traumatic stress disorder (PTSD), and treatment of psychological disorders. In one embodiment, the HMI has a patient-specific memory that records information about a patient's treatment pattern, which may include regimens that last over days, weeks or even months. In one embodiment, the HMI control application 55 periodically communicates through a wireless modem 56 with the facility's network storage servers 57 to automatically store and retrieve critical patient, operating and maintenance data. In another embodiment, the microprocessor 54 is connected to wide-area network 58 where TLLLT protocols can be updated remotely and periodic system maintenance can be automated. In another embodiment, physicians and technicians can input other patient observational information into the HMI control application that can provide feedback to researchers on the wide-area network (WAN) who develop and fine-tune TLLLT protocols. In one embodiment, the microprocessor 54, the HMI control application 55, the wireless modem 56 and the WAN connection 56 are all incorporated into the power supply 52. In another embodiment, a simplified power supply 52, connector cable 51 and head cover 20 is provided that requires virtually no training to operate and can be affixed to the patient or the patient's transportation vehicle for rapid initial TLLLT treatment while the ischemic patient is moved to a hospital or specialized treatment center where they can undergo more intensive TLLLT treatment regimens and receive better medical care than first responders may equipped to provide.

While light emitting diodes and lasers have been described herein as the light sources utilized in the head cover, other light sources are contemplated without departing from the scope of the current disclosure. For example, fiber optic cables (or a fiber optic network) may be used to transport light from an external light source to the inside of the head cover. The external light source may itself be a laser, light emitting diode, or other appropriate light source that has therapeutic value to the individual being treated. An important aspect of the light source is that it emit light at the appropriate wavelength and intensity at or near the surface of the head of the individual to provide the most efficient and effective treatment.

Particular embodiments of the current disclosure provide for light wavelengths of 730-770 nm, 760-860 nm, 808 nm, 850-890 nm, 880-920 nm, or 930-970 nm, each inclusive. Exemplary light emitting diodes include Si, GaAs and CdSe. Current range-finding LEDs (pulse operation) are capable of producing 905 nm light at peak power rates of up to 100 Watts (see Excelitas Technologies PGEW Series of multi-epi semiconductor lasers). Other LEDs include Everlight HIR323C, 850 nm+/−45 nm, Excelitas PGEW1SXXH, 905 nm+/−15 nm, Kingbright WP7113SF7C, 850 nm+/−50 nm, Mouser 15400385A3590, 850 nm+/−40 nm.

The current disclosure also provides for beneficial methods of treating individuals. A single treatment within 24 hours has a positive benefit; multiple treatments to photomodulate at different stages of the ischemic cascade also has positive benefits. Starting 2 hours after an ischemic event, 6 minutes of exposure provides for positive benefits at 7.5 mW/cm2 and 808 nm. In another embodiment, triple exposure of 2 minutes at 2 hours, 3 hours, and 4 hours at 111 mW/cm2 and 100 Hz results in a benefit to the individual. Early exposure gives more benefit, but may over time after the ischemic event.

In one example of the method of using the device, the following steps occur: removing hair from the head of an individual; placing a head covering device of the present disclosure on the individual's head, the device comprising an inside facing the head of the individual, the inside comprising a plurality of light sources; and activating the plurality of light sources to irradiate the head of the individual with light emanating from the plurality of light sources. In one example, the individual's head does not need to be shaved. In one example, the light emanating from the plurality of light sources has a wavelength of between 700 nm and 1000 nm inclusive. In one example, the power density of the light emanating from the plurality of light sources is between 200 mW/cm2 and 600 mW/cm2. In one example of the method, there is an additional step comprising administering tissue plasminogen activator (tPA) to the individual either before, during, or after irradiating the head of the individual. tPA is a protein that is well-known for breaking down blood clots by acting as an enzyme that catalyzes conversion of plasminogen to plasmin, plasmin being an enzyme that catalyzes breakdown of blood clots. When this additional step is added to the method of using the device disclosed herein, each of the effects of tPA and the device are augmented because the device is able to provide energy to the brain while the tPA is breaking down the blood clot. The additional energy provided by the device to the individual's cells allows them to survive while the tPA activates a long term solution by breaking up the clot.

In another example of the method, there is an additional step comprising inserting a catheter into a blood vessel of the individual to physically remove a blood clot. When this additional step is added to the method of using the device disclosed herein, each of the effects of the catheter and the device are augmented because the device is able to provide energy to the brain while the catheter is able to physically remove the blood clot. The additional energy provided by the device to the individual's cells allows them to survive while the catheter provides a long term solution by physically removing the clot. In one embodiment, the catheter is fiber optic and simultaneously irradiates the blood vessel and physically removes the clot. One example of a fiber optic catheter is a fiber optic tube, having an outside facing wall that transmits light between 700 nm and 1000 nm inclusive.

In another example of the method, both additional steps comprising administering tPA and inserting a catheter are employed before, during, or after using the device for the reasons described above.

That which is claimed:

1. An apparatus for treating ischemic stroke on a patient comprising:

a flexible substrate that is stretchable outward up to 0.25 inches with an effective spheroid radius of between 4.1 and 4.7 inches comprising a plurality of light sources embedded therein, said plurality of light sources capable of emitting light at a wavelength range of between 700 nm and 1000 nm inclusive and a radiant intensity range of between 200 mW/cm2 and 600 mW/cm2 inclusive;

wherein the flexible and stretchable substrate is configured to symmetrically cover a user's entire cranium, hold the plurality of light sources and relieve point-pressure caused by the plurality of light sources such that the light emits onto the entire cranium's surface; the plurality of light sources arrayed about each lobe of the entire cranium of the patient and emitting at least 3 different wavelengths within the wavelength range;

a multi-layer high-density interconnect printed circuit board comprising:

a plurality of rigid printed circuit board segments that are connected together using flexible conductor boards, wherein said circuit board is adjacent and operably connected to the flexible and stretchable substrate so that the circuit board can expand with the flexible and stretchable substrate, said circuit board having at least one pair of light emitting diode terminals soldered to at least one conducting strip;

microvias for receiving said terminals within the interconnect printed circuit board;

at least one lead wire, common ground wire and power supply;

wherein at least one of the pair of terminals for the each light emitting diodes is connected to the at least one lead wire that connects to the at least one power supply; and at least one of the pair of terminals is connected to the at least one common ground that returns the current flow back to the power supply; and a programmable controller operably connected to each light source within said plurality of light sources and configured to control the specific parameters of emitting light at the wavelength range of between 700 nm and 1000 nm inclusive and the radiant intensity range of between 200 mW/cm2 and 600 mW/cm2 inclusive to simultaneously irradiate both ischemic cells to stabilize their biofunction and healthy tissues to accelerate the natural revascularization process.

2. The apparatus of claim 1, wherein the programmable controller is an external power supply.

3. The apparatus of claim 1, wherein the plurality of light sources is a fiber optic network transporting light from one or more external light sources.

* * * * *